United States Patent [19]

Barry

[11] 4,265,246
[45] May 5, 1981

[54] STERILE COSMETIC SUTURE AND SCALP IMPLANT FOR ATTACHING HAIR PIECES

[75] Inventor: Robert J. Barry, Little Falls, N.J.

[73] Assignee: Barry Cosmetic Suture Company, Inc., Little Falls, N.J.

[21] Appl. No.: 43,651

[22] Filed: May 30, 1979

[51] Int. Cl.³ .............................................. A61B 17/00
[52] U.S. Cl. ..................................................... 128/330
[58] Field of Search ............ 128/330, 339, 325, 335.5; 3/1

[56] References Cited

U.S. PATENT DOCUMENTS

| | | | |
|---|---|---|---|
| 3,589,355 | 6/1971 | Lee | 128/303 R X |
| 3,877,570 | 4/1975 | Barry | 128/330 X |
| 4,050,100 | 9/1977 | Barry | 128/330 X |

*Primary Examiner*—Robert W. Michell
*Assistant Examiner*—Michael H. Thaler
*Attorney, Agent, or Firm*—B. P. Fishburne, Jr.

[57] ABSTRACT

A sterile needle with a trailing plastic tube receives telescopically and frictionally within the trailing tube a metal implant bushing sheathed in tissue compatible silicone rubber. A double headed wire extends through and beyone one end of the implant bushing. When the needle and trailing tubing are passed through the scalp for a sufficient distance to implant the silicone rubber sheathed bushing, the headed wire is held against movement of the bushing while the trailing tube is pulled off of the implanted bushing and separated from the scalp. A curved adapter needle may be employed in the initial penetration of the scalp. The silicone rubber sheathed bushing may be wired with or without a top bar for hair piece attachment.

3 Claims, 18 Drawing Figures

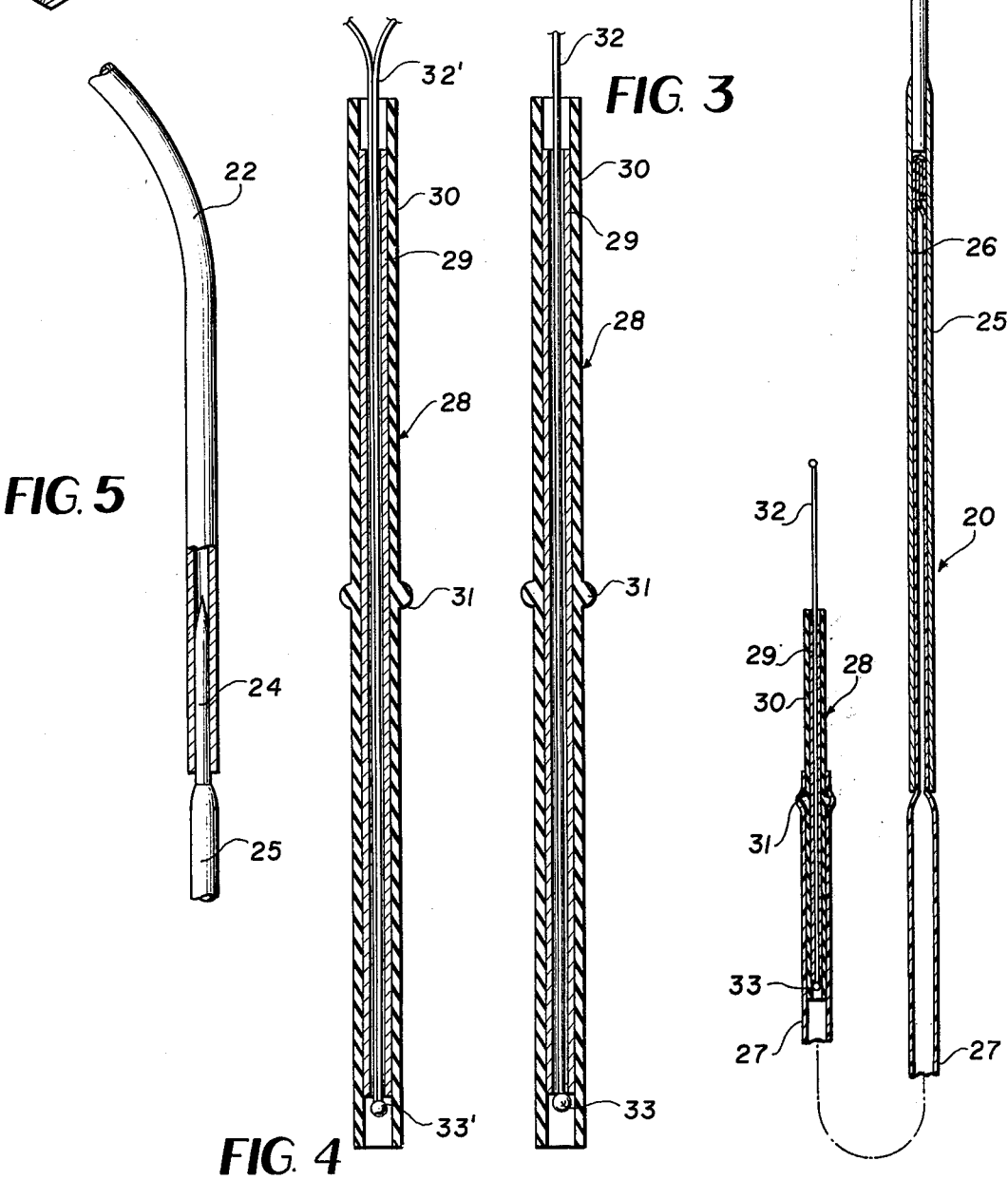

STERILE COSMETIC SUTURE AND SCALP IMPLANT FOR ATTACHING HAIR PIECES

BACKGROUND OF THE INVENTION

Essentially, the present invention is an improvement on the hair piece attaching means disclosed in U.S. Pat. No. 4,050,100, issued Sept. 27, 1977 to Robert J. Barry. That patent discloses a sterile needle and suture in the form of a teflon tube trailing the needle and encapsulating a stainless steel bushing which is permanently implanted in the scalp with a sheathing of teflon after cutting away and discarding the remainder of the teflon tubing and needle. End portions of the implanted bushing are bent upwardly from the scalp and are lock wired with a top bar to complete the formation of a hair piece anchor.

The present invention differs from the structure in U.S. Pat. No. 4,050,100 primarily in the provision of a soft tissue-compatible silicone rubber sheathing on the stainless steel bushing, which sheathing and bushing are partially telescoped in the rear end portion of the teflon tube trailing from the needle, and in the provision of a headed holding wire in the bushing and projecting from the rear end thereof to be grasped for holding the implanted bushing and silicone rubber sheathing stationary in the scalp as the needle and trailing teflon tube are pulled free of the bushing and scalp and discarded.

One end of the headed holding wire is cut away, and the wire is then pushed from the implanted bushing and discarded and a locking wire or wires can be employed at any subsequent time with or without a top bar in accordance with the teachings of U.S. Pat. No. 4,050,100.

Other features and advantages and modifications of the invention will be understood by those skilled in the art during the course of the following description.

BRIEF DESCRIPTION OF THE DRAWINGS

FIG. 1 is a composite perspective view of a sterile needle and suture-implant assembly and a curved adapter needle in sealed envelopes.

FIG. 2 is an enlarged needle and suture-implant assembly in cross section, partly broken away.

FIG. 3 is an enlarged fragmentary cross section taken centrally and longitudinally through the implant bushing and silicone rubber sheath and showing a headed holding wire within the bushing.

FIG. 4 is a sectional view similar to FIG. 3 showing a variant.

FIG. 5 is a fragmentary elevational view, partly in cross section, showing a curved adapter needle engaged telescopically with a straight needle.

DETAILED DESCRIPTION

Figure 6:
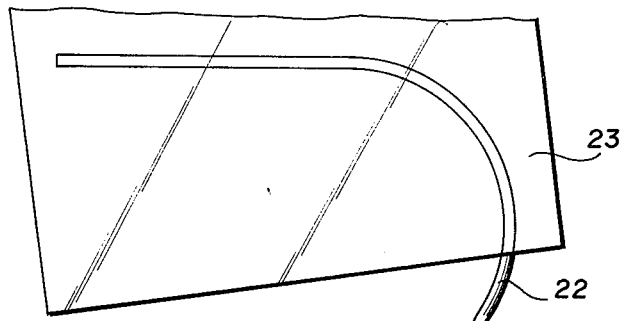
FIG. 6 is a partly schematic elevational view of the curved adapter needle showing its use in penetrating the scalp.

Referring to the drawings in detail wherein like numerals designate like parts, a sterile suture and scalp implant assembly 20, FIG. 2, is sealed inside of a sterile envelope 21, FIG. 1, in accordance with the teachings of U.S. Pat. No. 4,050,100. The envelope may also contain an implant top bar and a suitable length of locking wire for the same, not shown. A curved adapter needle 22 is provided in a separate sealed envelope 23 also in a sterile state, FIG. 1.

The suture and implant assembly 20 comprises a straight needle 24 secured within the forward end of a straight tubular shank 25 containing snugly the forward end portion 26 of a trailing flexible preferably teflon tubular suture 27 of the required length. This tubular suture may be anchored in the tubular needle shank in accordance with the teaching of U.S. Pat. No. 4,050,100.

The trailing end of tubular suture 27 receives snugly and telescopically therein a scalp implant 28 which consists of an interior straight preferably stainless steel bushing 29 and an external sheath 30 of soft pliable silicone rubber of a type sold under the trademark SILASTIC by Dow Corning or an equivalent material. The sheath 30 is a medical grade silicone rubber which is very compatible with human tissue. Its softness and stretchability promotes comfort in the scalp implant, is convenient for the installer of the implant, is self-anchoring in the scalp and enables an improved method of implantation, to be described. The silicone rubber implant sheath is a very important element of the invention and forms a significant improvement over the prior art. It would not be possible to implant it because of its elasticity except for the use of the teflon suture which encompasses it and which is discarded after its work is done.

As best shown in FIGS. 1 and 2, roughly one-half the length of the implant 28 is telescoped and frictionally held in the plastic suture 27, with the ends of the sheath 30 projecting slightly beyond the ends of the metal bushing 29. While not essential, an external enlargement 31 is preferably formed on the implant sheath 30 at its longitudinal center to promote anchorage in the scalp after implantation, FIG. 10. Instead of the enlargement 31, if preferred, small flanges can be produced on the ends of the silicone rubber sheath 30, not shown. The enlargement 31 or end flanges are easily produced by application of an available SILASTIC medical adhesive composition which becomes integrally fused with the sheath 30 after application thereto in a known manner. The implant sheath 30 will tend to be self-anchoring in the scalp and also in the tubular suture 27 even without the enlargement 31 or end flanges on the sheath 30. Preferably, the trailing end portion of the tubular suture 27 will be expanded for a short distance longitudinally to assist in the placement of the implant 27 in the suture telescopically.

The assembly 20 includes another element, namely a length of wire 32 extending through the bushing 29 and well beyond the trailing end of the suture 27 and implant 28. This wire includes two heads 33 formed thereon at the forward and rear ends of the bushing 29. The wire 32 is freely slidable through the bore of the metal bushing and the heads 33 are of such size that they cannot enter and pass through the bore of the bushing. The purpose of the headed wire 32 will be fully described.

FIG. 4 shows a variant of the implant 28 wherein a thin wire 32' corresponding to the headed wire 32 may be knotted as at 33' between its ends to produce an enlargement or head which will not pass through the bore of the metal bushing 29.

Figure 7:
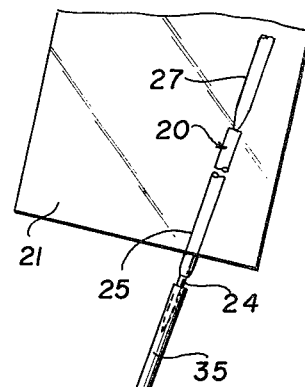
FIG. 7 is a further view, similar to FIG. 6, showing the curved adapter needle fully penetrating the scalp and the trailing engaged straight needle and suture, partly broken away.

With continued reference to the drawings, the method of installing the scalp implant 28 is as follows. First, the curved adapter needle 22, FIG. 6, is punctured through the sterile envelope 23 and is manipulated to penetrate through the scalp 34, as shown in FIG. 7. The curved adapter needle is particularly useful at the portions of the head which have minimum curvature. The needle 22 forms well defined spaced entrance and exit puncture openings in the scalp, as shown. The shank 35 of curved adapter needle 22 is tubular, and following insertion of the adapter needle in the scalp, FIG. 7, the straight needle 24 of the described assembly 20 is caused to pierce the sterile envelope 21 and is coupled telescopically with the shank 35. Following this coupling, the adapter needle 22 and the following straight needle 24, its shank 25, and the trailing tubular suture 27 containing the implant 28 are passed through the scalp tunnel generally according to the teaching of U.S. Pat. No. 4,050,100.

Figure 8:
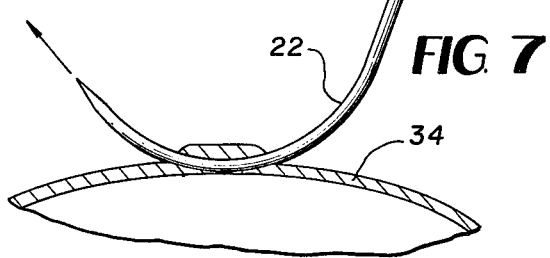
FIG. 8 is a fragmentary cross sectional view through the scalp showing the implanted bushing and silicone sheath with holding wire as the tube trailing from the straight needle is about to be pulled free.
Figure 9:
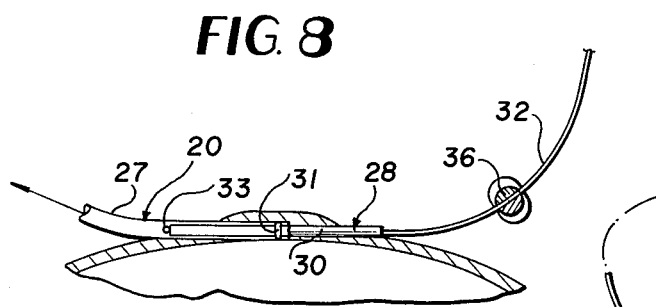
FIG. 9 is a similar section showing locking wire being passed through the implanted bushing.

Referring to FIG. 8, when the assembly 20 is drawn through the scalp sufficiently far to center the implant 28 within the tunnel formed through the scalp by the adapter needle 22, the headed control wire 32 is grasped by tweezers 36 and held against movement while the trailing end portion of suture 27 is stripped from the implant 27 and completely separated from the scalp and discarded with the remainder of the assembly 20, leaving the implant 28 properly positioned and held in the scalp by friction between the scalp tunnel and the silicone rubber implant sheath 30. One end of the headed control wire 32 can be cut off and the wire can now be pushed forwardly through the implant bushing 29 and separated from the implant and discarded, leaving the implant located in the scalp in the manner shown in FIG. 9.

Figure 12:
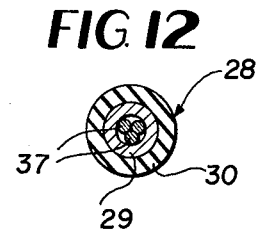
FIG. 12 is a transverse cross section taken on line 12—12 of FIG. 10.
Figure 10:
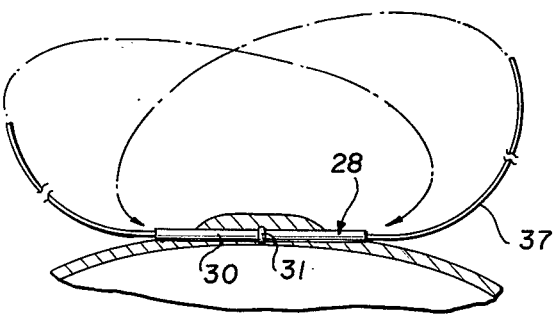
FIG. 10 is a similar cross section showing a completely wired bushing in accordance with the invention.

At any convenient time after implantation, each implant 28 can be wired with or without a top bar generally in accordance with U.S. Pat. No. 4,050,100. Prior to wiring the implant, FIG. 9, the excess end portions of the silicone rubber sheath 30 are cut off leaving the sheath ends flush with the ends of the metal bushing 29. Following this trimming, a lock wire 37 is threaded through the bushing 29 so that its ends project equidistantly from both ends of the bushing. Following this, a loop of wire 38 is formed above the implant 28 and the wire ends 39, FIG. 10, are threaded back through the bushing in opposite directions to close the loop. By pulling the wire ends, a loop of the desired size is produced and the excess wire end portions are flexed and broken off, leaving the structure approximately as shown in FIG. 10. No crimping or welding is required because a pull on the wire loop 38 radially of the skull will be firmly resisted without danger of pulling the wires from the bushing 29. Thus, the device is self-locking. This is because there are three strands of 0.005 inch diameter wire filling a 0.010 inch diameter bore of the bushing 29 snugly, as shown in FIG. 12. If the locking wire should break, it can easily be replaced any number of times.

Figure 11:
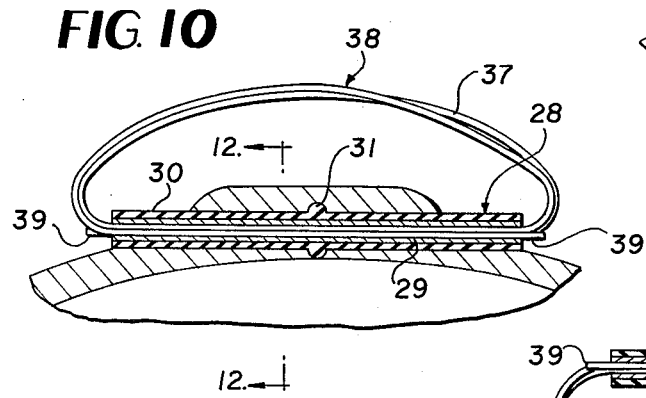
FIG. 11 is a cross section similar to FIG. 10 showing the implanted bushing wired in connected relationship to a floating top bar.
Figure 13:
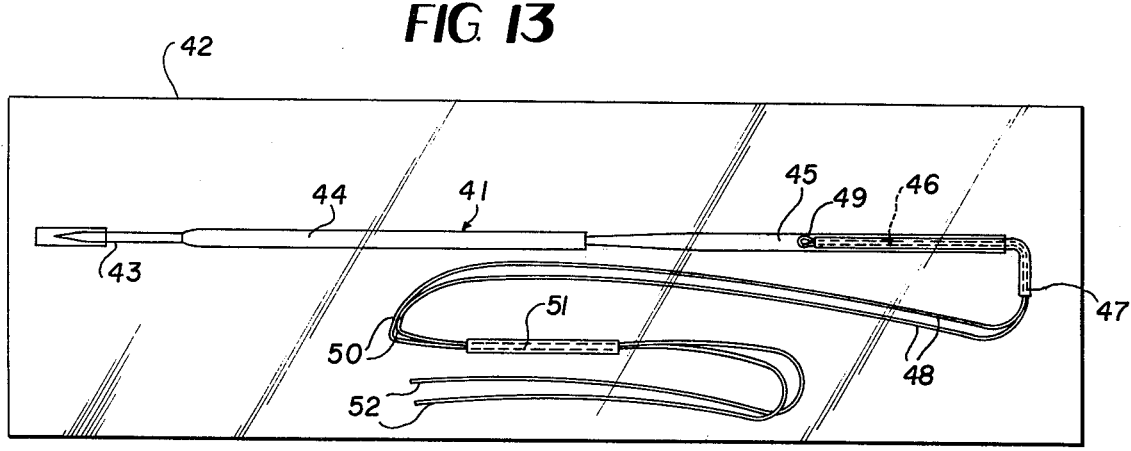
FIG. 13 is a plan view of a sealed sterile needle and suture-implant assembly according to a modification of the invention.
Figure 14:
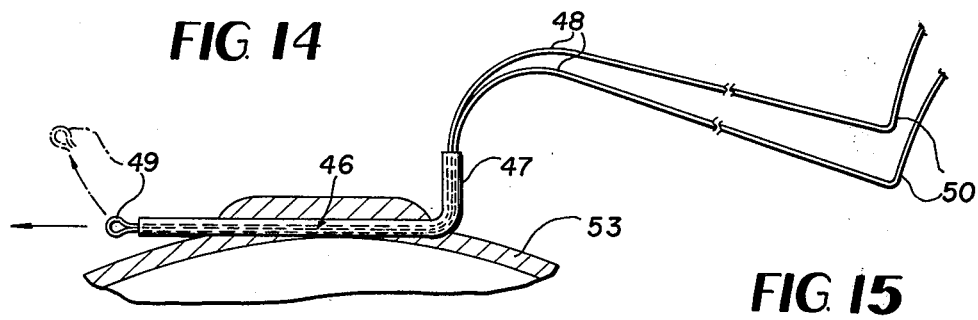
FIG. 14 is a fragmentary cross section of the invention in FIG. 13 following implantation.

FIG. 11 shows the invention where a top bar 40 is employed above the implant 28. In such instance, the wire loop 38 extends through the straight bore of the top bar 40, as illustrated and as disclosed in U.S. Pat. No. 4,050,100. The top bar 40 can be a teflon covered metal tube.

FIGS. 13 through 18 show a modification of the invention wherein a sterile needle, suture and implant assembly 41 is initially sealed in an envelope 42 for use with or without the previously described adapter needle 22. The assembly 41 comprises a needle point 43, tubular shank 44, and trailing teflon tube 45 which partially encapsulates an implant 46 including an interior stainless steel bushing.

The implant 46 is pre-bent to provide one right angular extension 47 thereon at its rearward end. A dual strand locking wire 48 is assembled in the implant, as shown, with the wire loop 49 disposed at one end of the implant and the lock wires projecting for some distance beyond its bent extension 47 and being abruptly pre-bent at distall points 50. Beyond the points 50, a top bar 51 similar to the bar 40 is pre-assembled on the lock wire strands 48 whose free ends 52 extend for some distance beyond the top bar.

Figure 15:
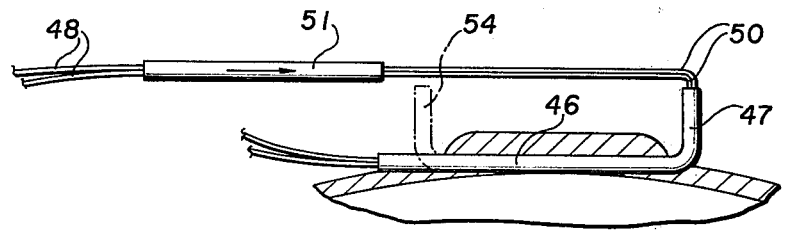
FIG. 15 is a further cross sectional view similar to FIG. 14 showing the completion of formation of the implant bushing and the wiring thereof with a top bar.
Figure 16:
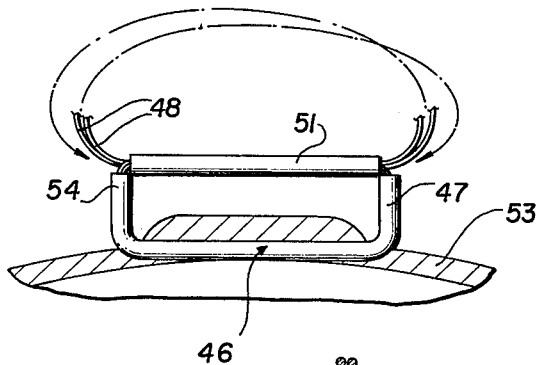
FIG. 16 is a further view similar to FIGS. 14 and 15 showing a further part of the wiring procedure.

In the implantation procedure, the scalp 53 is pierced in the previously-described manner by means of the needle 43 alone or in conjunction with adapter needle 22. When the straight needle and trailing teflon tube 45 are pulled through the scalp tunnel, the pulling movement continues without reciprocation until the pre-bent extension 47 of the implant reaches the entrance opening formed in the scalp. The arrangement forms an automatic gage or stop on the implant 46 to assure its proper positioning in the scalp, and the teflon is cut. All of this has occurred in FIG. 14 and the removal of the teflon suture tube is indicated by the solid directional arrow in FIG. 14. Following this, the wire loop 49 is grasped and pulled so as to draw the wire strands 48 through the bore of the implant metal bushing up to the point shown in FIG. 15 where the bends 50 meet the upturned end of the extension 47 which again forms an automatic gage or stop. This last wire pulling procedure is indicated by the broken arrow in FIG. 14 and by the directional arrow in FIG. 15. Following this procedure, the other end portion of the implant 46 is bent upwardly as at 54 into parallel relationship with the extension 47 and this establishes the final and proper positioning of the teflon covered implant or bushing in the scalp. Following such final bending of the implant 46, the top bar 51, FIG. 15, is slid along the wire strands 48 toward the bends 50 to the proper position between the extensions 47 and 54 and parallel to the base of the implant, as shown in FIG. 16.

Figure 17:
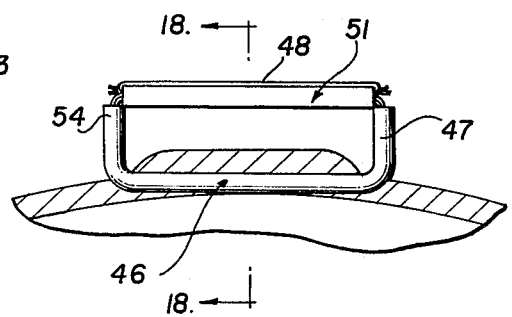
FIG. 17 is a similar view showing the top bar completely wired to the sheathed implant bushing.
Figure 18:
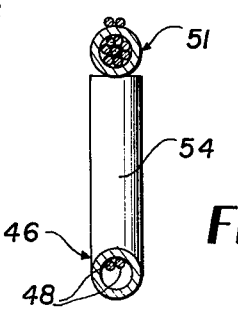
FIG. 18 is an enlarged transverse vertical section taken on line 18—18 of FIG. 17.

With the above accomplished, the small loop 49 can be cut off of the wire strands which now extend through the implant 46 and top bar 51 and the wire ends are back-threaded through the top bar 51 and pulled to draw the bar 51 into tight relationship with extensions 47 and 54. Finally, the wire ends, after overbending, are threaded back through the top bar 51 to fill the bore of the top bar with eight wire strands, as shown in FIG. 18, two strands lying on the outside of the top bar 51, as shown in FIGS. 17 and 18. Again, no crimping or welding of the locking wire is required for the reason previously explained. The subsequent fastening of wefts of hair to the implant top bar serves further to entrap the wire and thus preventing involuntary unthreading. The final excess free end portions of wire need only be flexed and broken off. Variations in the wiring procedure with or without a top bar may be resorted to, in some cases.

It should now be apparent to those skilled in the art that the invention as disclosed possesses the following advantages, among others:

1. It is packaged to maintain a constant sterile environment around the implant up to its final locating in the scalp.

2. Each needle and suture assembly is used only one time.

3. Surgery consists of installing the implant in a medically prepared scalp by a single straight through nonreciprocating penetration.

4. Final installation of the double lock wire or top bar and lock wire may be done any convenient time after surgery.

5. The implant provides automatic locking without crimping or welding against any pull generally radially of the skull.

6. The implant has a unique floating action and its small movements are not transmitted as stresses to the scalp, but rather are absorbed inside the stainless steel bushing. Only direct pulls will be transmitted to the scalp.

It is to be understood that the forms of the invention herewith shown and described are to be taken as preferred examples of the same, and that various changes in the shape, size and arrangement of parts may be resorted to, without departing from the spirit of the invention or scope of the subjoined claims.

I claim:

1. A needle, suture and scalp implant assembly comprising a needle adapted to penetrate the scalp generally tangentially of the skull for forming entrance and exit scalp openings, a trailing flexible tubular tissue-compatible suture connected with the needle, a tubular scalp implant bushing engaged telescopically and frictionally in the bore of said suture, said implant bushing having a metal tube body and an exterior sheath of soft compliant tissue-compatible silicone rubber covering the entire exterior surface of the metal tube body and fixed thereon, and elongated control element of greater length than the implant bushing extending movably through the bore of the metal tube body of the implant bushing and trailing from the implant bushing and suture, an enlarged head at each end of said elongated control element, the heads of said control element being larger than the bore of the metal tube body and incapable of passing through said bore, whereby after positioning of the implant bushing in the scalp the control element may be held to prevent axial displacement of the implant bushing while the tubular suture is pulled from the silicone rubber covering of the implant bushing.

2. A needle, suture and scalp implant assembly as defined in claim 1, and an external enlargement on the silicone rubber covering of the implant bushing near its longitudinal center serving to further anchor the implant bushing within the scalp, the enlargement also being formed of said silicone rubber.

3. A needle, suture and scalp implant assembly as defined in claim 1, and said tubular tissue-compatible suture comprising a Teflon tube.

* * * * *